United States Patent [19]

Dyroff et al.

[11] Patent Number: 5,185,485

[45] Date of Patent: Feb. 9, 1993

[54] PROCESS FOR PREPARING ALKYLBENZENE

[75] Inventors: David R. Dyroff; Prakasa R. Anantaneni, both of St. Louis, Mo.

[73] Assignee: Monsanto Company, St. Louis, Mo.

[21] Appl. No.: 722,785

[22] Filed: Jun. 28, 1991

[51] Int. Cl.$^5$ .............................. C07C 2/64
[52] U.S. Cl. .................. 585/446; 585/646; 585/823; 585/323
[58] Field of Search .................. 585/646, 823, 323

[56] References Cited

U.S. PATENT DOCUMENTS

| | | | |
|---|---|---|---|
| 2,347,945 | 5/1944 | Frey | 260/683.4 |
| 2,377,546 | 6/1945 | Frey | 196/44 |
| 2,391,149 | 12/1945 | Frey | 196/41 |
| 2,403,714 | 7/1946 | Frey | 260/683.4 |
| 2,409,372 | 10/1946 | Matuszak | 585/823 |
| 2,626,967 | 2/1951 | Darragh et al. | 585/823 |
| 2,645,672 | 7/1953 | Schulze | 260/671 |
| 2,932,677 | 4/1960 | Kirk et al. | 260/674 |
| 3,058,800 | 10/1962 | Frevel et al. | 23/2 |
| 3,265,757 | 8/1966 | Frevel et al. | 260/677 |
| 3,338,983 | 8/1967 | Thompson | 260/674 |
| 3,446,867 | 5/1969 | Kerfoot et al. | 260/671 |
| 3,454,666 | 7/1969 | Jacobs et al. | 260/674 |
| 3,474,154 | 10/1969 | Yamanaka et al. | 585/323 |
| 3,494,971 | 2/1970 | Fenske | 260/671 |
| 3,538,175 | 11/1970 | Hervert | 585/323 |
| 3,864,243 | 2/1975 | Reusser et al. | 585/823 |
| 4,072,730 | 2/1978 | Winter, III | 260/671 |
| 4,433,196 | 2/1984 | Yang et al. | 585/823 |
| 4,463,205 | 7/1984 | Spinner | 585/455 |
| 4,468,476 | 8/1984 | Yang et al. | 502/83 |
| 4,491,516 | 1/1985 | Polleck et al. | 208/248 |
| 4,523,048 | 6/1985 | Vora | 585/323 |
| 4,691,068 | 9/1987 | Resh | 585/323 |
| 4,835,338 | 5/1989 | Liu | 585/823 |

OTHER PUBLICATIONS

Vora, Bipin, et al.–"Production of Detergent Olefins and Linear Alkylbenzenes" Chemistry Industry, pp. 187–191, Mar. 19, 1990.
Product Bulletin–LaRoche Chemical Co., 1988.

*Primary Examiner*—Asok Pal
*Assistant Examiner*—C. Everhart
*Attorney, Agent, or Firm*—Raymond C. Loyer; Richard H. Shear; James C. Polding

[57] ABSTRACT

There is disclosed an improved process for the production of linear alkylbenzene wherein monoolefins are reacted with benzene in a hydrogen fluoride catalyzed reaction followed by recovery of the alkylbenzene. An alumina treatment step is included which removes organic fluoride impurities in order to prevent release of hydrofluoric acid in downstream equipment. It has been discovered that the $SO_3$ sulfonation color of the alkylbenzene is surprisingly improved by the use of a high selectivity basic alumina for this treatment.

29 Claims, No Drawings

PROCESS FOR PREPARING ALKYLBENZENE

This invention relates to a process for preparing detergent range alkylbenzene and more particularly to an improved process wherein the alkylation product from a hydrogen fluoride catalyzed alkylation reaction is treated with a basic alumina providing advantages in both capital cost of the manufacturing plant and quality of the alkylbenzene.

BACKGROUND OF THE INVENTION

The commercial scale production of detergent range (C9-C15 side chain) linear alkylbenzene (LAB) by a process which includes a step in which benzene is alkylated by linear monoolefins (MO) in the presence of hydrofluoric acid (HF) is known. In such a process, a mixture containing MO is contacted with excess benzene under suitable alkylation conditions to form LAB. Most of the HF is allowed to settle out as a separate HF rich liquid phase which is removed for recycle, and the remaining hydrocarbon rich liquid phase is then subjected to a series of fractionation (distillation) steps, optionally accompanied by one or more additional purification steps, in order to recover LAB of acceptable purity and also recover various species such as unconverted benzene and further amounts of HF for recycle. As used herein, the term "HF-LAB process" refers to a process of the type described above. It is also known to employ in an HF-LAB process a mixture containing MO produced by the dehydrogenation of the corresponding normal paraffins (NP). Such a mixture is produced by contacting a mixture containing NP under dehydrogenation conditions with a suitable catalyst such as platinum, resulting in partial conversion of the NP to MO. The resulting mixture is optionally concentrated and/or purified by one or more means such as distillation, selective hydrogenation, selective adsorption, etc. prior to use in the alkylation step. As used herein, the term "Dehy-HF process" refers to an HF-LAB process in which such a dehydrogenation mixture is used as the MO source. Usually in a process of this type, the mixture contacted with benzene contains both MO and a substantial amount of unconverted NP, in which case a distillation step is included to recover unconverted NP for recycle.

It is known that hydrocarbon mixtures as initially produced by any HF catalyzed alkylation process are usually contaminated by trace amounts of organic fluoride impurities (RF). The RF often includes species covering wide ranges of thermal stability and boiling point. Thus, as such a mixture is fractionated, objectionable amounts of both RF and HF formed by the thermal or catalytic decomposition of RF tend to be present in many if not all locations of the process downstream of the alkylation step, possibly including various recycle streams. A known method of greatly reducing this widespread migration of RF and widespread generation of HF is to include in the process at one or more locations a step herein referred to as "alumina treatment". In such a step, after separating most or all of the HF initially present in the alkylation mixture, either the entire remaining reaction mixture or one or more fractions of it are contacted with alumina under conditions sufficient to result in removal of most of the RF and HF. Such a method is described for example in U.S. Pat. No. 2,347,945.

In the production of LAB by the Dehy-HF process without the use of some method of RF removal such as alumina treatment, widespread migration of RF occurs to an extent sufficient to result in a number of significant disadvantages. One such disadvantage is fluoride contamination of the dehydrogenation catalyst resulting from its contact with RF or HF contained in recycled NP. Typically, the dehydrogenation catalyst includes an alumina support, and as such contamination increases, a point is soon reached such that the resulting acidic sites on the alumina support catalyze side reactions such as hydrocarbon cracking and isomerization to an objectionable extent. At this point one must choose between toleration of these side reactions or replacement of the dehydrogenation catalyst at considerable expense. Other disadvantages of widespread RF migration are associated with the resulting widespread breakdown of RF with the release of HF. Such disadvantages include increased corrosive attack upon processing equipment, the need to use more costly corrosion resistant materials of construction to keep such corrosive attack within acceptable limits, contamination of product and byproduct streams with HF, and increased risk of exposure of plant operating and maintenance personnel to HF.

In order to reduce the problems associated with widespread RF migration in the production of LAB by the Dehy-HF process, one or more alumina treatment steps are typically included. For purposes of minimizing such problems, the most advantageous approach is to employ a single alumina treatment step located immediately after the separation of the HF from the alkylation mixture. For example, if a single distillation column is used to recover both the dissolved HF and the unconverted benzene, an alumina treater including one or more stages can be located in the stream recovered from the bottom of this column. Such location minimizes the adverse effects of RF in all downstream equipment involved in the fractionation and purification of the alkylation mixture. Since such downstream equipment includes the paraffin recovery column, RF is also greatly reduced in the recycle paraffin stream, and this protects the dehydrogenation catalyst from excessive exposure to RF.

However, in previously known Dehy-HF processes, it has been found that exposure to the alumina treatment step of the alkylation mixture fraction having a higher boiling range than the unconverted benzene has resulted in a large adverse effect upon the quality of the LAB produced. This adverse effect is most apparent when such LAB is sulfonated using SO3 (as distinguished from oleum) in the production of detergents. The sulfonated product contains such a high level of darkly colored materials that it is difficult to use it to produce detergent formulations of acceptable appearance. As used herein, the term "SO3 sulfonation color" refers to the degree to which the LAB has the tendency to produce such darkly colored SO3 sulfonation products.

It has been found that if only the recycled NP stream is subjected to alumina treatment, adverse effects of alumina treatment upon the quality of the LAB can be largely avoided. Production of LAB by a Dehy-HF process in which the alumina treatment step is located in the recycle paraffin stream is widely practiced (B. Vora et al, Chemistry & Industry, 19 Mar., 1990, pp. 187-191). Such processes are known to be capable of producing LAB of good quality, but they suffer from the disadvantages of allowing higher levels of RF and HF within the paraffin recovery column and all downstream equipment. Such downstream equipment must be fabricated to withstand the highly corrosive effects of HF resulting in higher capital costs, and the presence of HF within this equipment results in greater risk of exposure of plant workers to HF.

BRIEF DESCRIPTION OF THE INVENTION

The present invention provides an improved HF-LAB process which results in an advantageous combination of LAB quality, operating costs, and operating safety. In this process, RF is effectively removed from a process stream comprising crude alkylbenzene by treating said stream under suitable alumina treater conditions with a high selectivity basic alumina. As used herein the term "crude alkylbenzene" refers to the fraction of the above mentioned hydrocarbon rich liquid phase with a boiling range higher than that of the corresponding NP.

As used herein, the term "high selectivity basic alumina" refers to a basic alumina which is able to effectively remove RF and which also passes the alumina selectivity test described in detail below which measures its tendency to degrade the quality of the LAB. A considerable variety of basic aluminas are commercially available. Some but not all basic aluminas qualify as high selectivity basic aluminas for use in the process of this invention.

The treatment of the crude alkylbenzene with the high selectivity basic alumina can occur at any point in the process after the removal of the HF from the alkylation mixture and either before or after separation of the crude alkylbenzene from such lower boiling species as unconverted benzene and/or NP. While in the prior art, exposure of the crude alkylbenzene to alumina treatment has had a large adverse effect upon the quality of the LAB, it has now been surprisingly discovered that such treatment can be accomplished in the process of this invention with little if any such adverse effect upon the LAB by limiting the alumina treatment of the crude alkylbenzene fraction to treatment with high selectivity basic alumina.

Thus, in accordance with this invention, there is provided an improved process for producing detergent range linear alkylbenzene by (1) reacting the corresponding monoolefins with benzene in the presence of hydrofluoric acid catalyst to form an alkylation mixture, (2) removing the hydrofluoric acid to obtain a hydrocarbon mixture, (3) recovering crude alkylbenzene from said hydrocarbon mixture, and (4) purifying the crude alkylbenzene to obtain the linear alkylbenzene, wherein the improvement comprises contacting at least a portion of said hydrocarbon mixture comprising crude alkylbenzene under RF removal conditions with a basic alumina having a bromine number ratio not greater than about 1.25 in the alumina selectivity test.

DETAILED DESCRIPTION OF THE INVENTION

As used herein, the term "neutral alumina" refers to an activated alumina containing no deliberately added amounts of alkali metal and/or alkaline earth metal compounds and relatively low total amounts of such compounds. Typical neutral aluminas such as those produced by LaRoche Chemicals under the product codes A-201 and A-202(HF) contain one or more sodium compounds which are derived from the raw materials used to produce them and which provide a total sodium content equivalent to roughly 0.35 wt. % $Na_2O$. This small amount of alkali metal is insufficient to impart a substantial degree of basic character to the alumina.

As used herein, the term "basic alumina" refers to an activated alumina which either contains deliberately added amounts of one or more alkali metal and/or alkaline earth metal compounds or for whatever reason contains amounts of such compounds equivalent to at least about 0.5 wt. % as the oxide of the corresponding basic metal. When the term "basic metal" is used herein in the description of a basic alumina, it refers to an alkali metal, an alkaline earth metal, or combinations thereof.

The term "activated alumina" refers to an alumina with relatively high internal surface area, typically about 200 square meters per gram or higher. The term "activation" refers to the heat treatment normally used to create the high internal surface area of an activated alumina or to drive off water or other volatile species from an activated alumina.

When an alumina is described herein as containing a certain amount of a basic metal or its oxide, this means only that it contains the equivalent amount of one or more compounds of the basic metal, and such description is not intended to place any limitation on which particular compounds of the basic metal are included.

Basic aluminas, methods for their preparation, and various applications of basic aluminas have long been known in the art. In U.S. Pat No. 2,391,149, a process is described for removal of RF from hydrocarbon mixtures by contacting with a silica-containing alumina impregnated with an alkali metal hydroxide. The stated purpose of the alkali metal hydroxide is to react with liberated HF and avoid contamination of the treated product by silicon-fluorine compounds. This avoids any need to use more costly grades of alumina with lower silica contents. Other basic aluminas, their preparation, and their use in the removal of carbonyl sulfide (COS) from hydrocarbon streams are described in U.S. Pat Nos. 3,058,800; 3,265,757; 4,491,516; and 4,835,338.

The process of this invention requires the use of a high selectivity basic alumina. A number of grades of basic alumina are commercially available, and an unlimited number of basic aluminas of varying composition and structure are possible. The alumina selectivity test described below has been found effective for use in identifying which of these aluminas qualify as high selectivity basic aluminas useful in the process of this invention.

A high selectivity basic alumina as defined herein must have a Br No. Ratio no greater than 1.25 in the alumina selectivity test described herein. In the event that it is not possible at some time in the future to perform the test exactly as described (due for example to unavailability of the indicated control grades or a substantial change in the properties of these grades), it should be understood that a test providing equivalent determinations of Bromine No. Ratio may be employed. In any case, the ability to pass the test by a larger margin (with a lower Br No. Ratio) is preferred since that is expected to result in higher LAB quality. Thus, it is preferred to use a high selectivity basic alumina with a Br No. Ratio not greater than about 1.00.

Any combination of alkali metal compounds and alkaline earth metal compounds can be used in the high selectivity basic alumina so long as its resulting properties meet the requirements specified herein. It has been found that basic aluminas in which the basic metal is alkali metal tend to give better test results (smaller Br No. Rise) than those in which the basic metal is alkaline earth metal. It has also been found that test results tend to improve as the content of alkali metal increases, at least up to about 4% $Na_2O$ in the case that the alkali metal is sodium. Greatly higher levels of alkali metal tend to have adverse effects upon other properties of the alumina such as crush strength. Basic aluminas containing sodium tend to be lower in cost and more widely available than those containing other added alkali metals.

For these reasons it is preferred to use a basic alumina in which the basic metal is alkali metal, and more preferred to use a basic alumina in which the basic metal is sodium. When the basic metal is sodium, it is especially preferred that the amount be within the range of from about 3 wt. % to about 5 wt. %, expressed as $Na_2O$. An especially preferred basic alumina is Alcoa's Selexsorb COS grade since studies have shown it to perform somewhat better than other grades in the alumina selectivity test.

A high selectivity basic alumina as defined herein must also be able to effectively remove RF from the LAB process streams that it is used to treat. This means that its use under appropriate RF removal conditions in a well designed fixed bed alumina treater containing a large excess of the alumina will provide during the early part of the alumina bed life an effluent F level that is low enough to avoid significant problems due to RF in downstream equipment. It is expected that this requirement will be met by many if not all basic aluminas presently available in commerce, and the requirement is in any case considered to be met by the basic alumina if the resulting downstream RF level is not substantially greater than that obtained under the same conditions using the same amount of a typical neutral alumina useful for RF removal (such as the LaRoche A-202HF grade). Appropriate conditions for RF removal include an alumina bed temperature of at least about 200° C. and preferably at least about 230° C. It has been found that some grades of basic alumina are essentially equal to neutral alumina in their ability to remove RF. Moderate differences in the ability to remove RF can be offset if desired by adjustment of bed size.

Preferred high selectivity basic aluminas for use in the process of this invention will also possess various other properties well known in the art to be desirable for the practical operation of an alumina treater. Such properties include suitable pellet strength, suitable thermal stability, low levels of any impurities that would adversely affect the process, and a suitable particle size distribution in the range employed traditionally to remove RF from hydrocarbon streams. It has been found that high selectivity basic aluminas are available which are acceptable in all respects. The optimum combination of properties for use under any particular desired process conditions can be determined by routine experimentation in view of the present disclosure.

The method of preparation of high selectivity basic aluminas for use in the process of this invention is not important except to the extent that it affects important properties of the alumina. One aspect of the method of preparation is the choice of the particular compound used for incorporation of a basic metal into the alumina. It is preferred that this basic metal compound be an oxide or a compound decomposable to an oxide so that no undesirable residual materials are left in the alumina after activation. Examples of such compounds include hydroxides, carbonates, and nitrates. However, other compounds such as stable salts of strong acids may be present provided that such compounds do not interfere with the performance characteristics specified herein.

Within the scope of this invention, considerable variation is possible in the selection of the process stream or streams to be alumina treated. In one preferred embodiment, only one stream is treated, that being the stream emerging from the bottom of the benzene recovery column. Alternatively, if the process is arranged so that there is a stream which still contains a substantial amount of benzene but from which essentially all of the dissolved HF has been removed, that stream can be the sole stream to be alumina treated. In the Dehy-HF process, if an alumina treater is not provided prior to the paraffin recovery column, at least two streams must be treated to provide a high degree of protection against the adverse effects of RF and HF, one of these being the NP recycle stream. A preferred embodiment of this type provides a treater using lower cost neutral alumina in the NP recycle stream and a treater using high selectivity basic alumina in the paraffin column bottoms stream. Regardless of the number and location of streams selected for alumina treatment, it is preferred that high selectivity basic alumina be used for all treated streams which contain significant amounts of the crude alkylbenzene fraction of the alkylation mixture.

For each stream that is alumina treated, the treatment step can employ a single alumina bed or multiple beds in various arrangements. It is preferred to use two beds in series so that the first bed can be operated until fluoride begins to break through (i.e. F content of the effluent stream begins to rise fairly rapidly). In this arrangement, the second bed still provides protection during the period while breakthrough is being detected and while the spent alumina of the first bed is being replaced. For maximum protection, the fresher bed is always used in the backup position during operations with both beds in service. The amount of alumina in each bed is usually selected mainly on the basis of the desired bed life prior to replacement and can be varied widely.

It is preferred to employ fixed beds under conditions such that the treated stream is a liquid, although other modes of operation are possible. Such factors as the direction of flow, bed shape or L/D, operating pressure, and bed temperatures can also be varied widely. A lower bed temperature chosen from a range that provides effective removal of RF tends to provide better selectivity (lower Br No. Rise). Bed temperatures within the range of from about 200° C. to about 295° C. are preferred, and bed temperatures in the range of from about 230° C. to about 260° C. are especially preferred. Various conditions used may be the same or different for different beds, for different treated streams, and for operations on different feedstocks. Selections of the most favorable combinations alumina treater conditions can be determined by routine experimentation by one skilled in the art in view of the present disclosure.

The regeneration of alumina beds used for removal of RF from hydrocarbon streams has been described in U.S. Pat. No. 2,391,149. While it is possible to use such a method in the process of this invention, it is preferred to replace spent beds rather than regenerate them.

Many variations in the process are possible within the scope of this invention. For example variations in alkylation or dehydrogenation conditions, choices of raw materials, conditions used in distillation columns, number and types of distillation columns, and inclusion of various optional steps are possible within the scope of this invention. Another variation within the scope of this invention is the source of linear monooleffins. Such sources include, but are not limited to, olefins derived from the dehydrogenation of normal paraffins, linear monoolefins derived from other processes and mixtures thereof. The practice of this invention is not limited to any particular choices of such variables.

One of the significant benefits of the present invention is the ability to produce LAB with a relatively low SO3 sulfonation color. This has become more important in recent years as users of LAB have increased their use of SO3 sulfonation processes for the conversion of LAB to its corresponding sulfonic acid. Many methods have been described for improvement of the purity and/or sulfonation color of detergent alkylates. It is expected that the benefits of one or more of these methods will be additive to a significant extent to the sulfonation color benefits of this invention.

The above mentioned methods include but are not limited to selective hydrogenation of dehydrogenation products prior to alkylation (U.S. Pat. No. 4,523,048), use of two or more distillation columns to separate the LAB from higher boiling species (U.S. Pat. No. 4,463,205 and U.S. Pat. No. 4,691,068), recovering the hydrocarbon phase of the alkylation mixture and subsequently contacting it with high purity HF (U.S. Pat. Nos. 3,494,971 and 4,072,730), selective hydrogenation of detergent alkylate (U.S. Pat. No. 3,454,666), treatment of detergent alkylate with various oxidizing agents (U.S. Pat. No. 2,932,677 and U.S. Pat. No. 3,338,983), washing of detergent alkylate with concentrated sulfuric acid (U.S. Pat. No. 3,446,867), and treatment of detergent alkylate with various clays and/or zeolites (U.S. Pat. No. 4,433,196 and U.S. Pat No. 4,468,476). The choice of whether to include one or more such methods in the practice of this invention depends upon the LAB SO3 sulfonation color required, the extra costs incurred for each method, and the degree of additivity of the sulfonation color benefits. For any particular situation, the most advantageous combination can be determined by routine experimentation.

ALUMINA SELECTIVITY TEST

The following procedure was employed to identify basic aluminas of the type referred to herein as high selectivity basic aluminas. The alumina to be tested was dried by heating overnight at about 177° C. followed by cooling in a desiccator. A portion of the dried alumina was then used to fill a cylindrical 316 stainless steel reactor six inches long and one inch in internal diameter which had a thermocouple well fitted to the discharge end. The reactor was immediately closed up and connected to the lines which supply the feed and remove the product. The long axis of the reactor was vertical and the feed flowed upward through the alumina bed. Bed temperature was controlled primarily by placement of the reactor in an oven. The feed line included about nine feet of $\frac{1}{8}$ inch stainless steel tubing which was coiled around the reactor and which served to preheat the feed. Heating tape was also provided around the reactor to supply extra heat when needed. The alumina was heated to a temperature slightly above that to be used in the selectivity test, and the feed pump was started. During the next hour, final adjustments were made to obtain steady operating conditions, and the first product sample was accumulated in a sample receiver. Subsequent samples were also accumulated over one hour intervals, and the total run time was either nine or ten hours. It was found that the results were not significantly different for various run lengths in this range. The feed material was obtained from a dehy-HF process operating at steady state to produce detergent range LAB and in which unconverted portions of the starting materials were being recycled. The feed material consisted of the portion of the alkylation mixture which remained following the removal of the HF catalyst and unconverted benzene. The feed material was fed to the reactor at the rate of six grams per minute. If the feed was obtained from a light feedstock process (employing NP with less than 5 wt. % C14), the bed temperature was about 260° C. during the test run. If the feed was obtained from a heavy feedstock process (employing NP with less than 5 wt. % C11), the bed temperature was about 288° C. during the test run. An intermediate temperature can be used in the unlikely event that the only available feedstock falls between light and heavy as defined above. Using the method described separately herein the Br No. Rise was determined by finding the bromine number (Br No.) for both the feed and the test reactor effluent samples. For each sample collected after reaching steady conditions, the increase in Br No. across the reactor was calculated, and these values were averaged to obtain a Br No. Rise value characteristic of the grade of alumina used in the run. The above procedure was repeated using the same feed type to determine values of Br No. Rise for the alumina under test and for either of the following commercially available grades of basic alumina as a control: LaRoche A204-1 5×8 mesh, Alcan AA-200S 4×8 mesh. As used herein the term "bromine number ratio (Br No. Ratio)" means the Br No. Rise of an alumina divided by the Br No. Rise of the control alumina. An alumina passes the test if its Br No. Ratio is not greater than about 1.25. For the feed materials used in developing the test, it has been found that the Br No. Ratio for the control grades is roughly half that for typical neutral aluminas such as LaRoche's A201 or A202HF grades.

DETERMINATION OF BROMINE NUMBER

The bromine numbers used to calculate values of the Br No. Rise discussed herein were determined by an electrometric titration method based upon ASTM Standard D2710-84. It should be noted that a Br No. is smaller by a factor of 1000 than the corresponding bromine index.

DETERMINATION OF SO$_3$ SULFONATION COLOR

The SO$_3$ sulfonation colors discussed herein were determined by the following procedure. About 0.2 mole of LAB was placed into a baffled glass reactor equipped with an agitator, feed and vent lines, and temperature readout. An air-SO$_3$ mixture was formed in a separate vaporizer operated at 50° C. or slightly higher, and added subsurface to the agitated sulfonation mass. The air flow rate was 3000 ml/min., and a total of 1.15 moles of SO$_3$ per mole of LAB was added to the vaporizer at a uniform rate such that the total addition time was in the range of 18-24 minutes. Using an ice bath, the temperature of the sulfonation mass was maintained in the range of 50°-55° C. during the addition. Following the addition, agitation was continued for 5 minutes, and the temperature of the mass was lowered to 40° C. Water equal to 2%, by weight, of the mass in the reactor was then added dropwise to the vortex of the agitated mass, followed by agitation for another 5 minutes. Within the next 5 minutes, a solution was prepared by dissolving 5 g of sulfonation mass in 95 g of water. The color of this solution was measured at a wavelength of 400–465 nm using a Klett-Summerson colorimeter with deionized water as the reference liquid.

DETERMINATION OF FLUORIDE CONTENT

Residual F contents of alumina bed effluents were determined by the following method. About 1 g of a dehydrogenation catalyst comprising Pt on an alumina support was placed in a Caldwell recycle reactor supplied by Autoclave Engineers, Inc., Erie Penna., and about 1000 g of the alumina bed effluent was fed through under the following reactor conditions:

Pressure—1.35 Atmos.
$H_2$/feed mole ratio—2.5
Feed rate—1.0–1.1 g/min.
Catalyst temperature—415°–420° C.
Impeller speed—2500 RPM As a result, most of the F in the feed was accumulated onto the catalyst providing about a 1000 fold increase in F concentration. The resulting catalyst sample was ground up, and 0.1 g weighed into a nickel combustion boat containing 0.3 g of vanadium pentoxide and 1.5 g of granular tin. This mixture was heated to 900°–1000° C. in a Lindbergh furnace in the presence of steam. The resulting combustion products were trapped in about 10 ml of 0.04%, by weight, aqueous NaOH solution. The F content of an aliquot of this solution (buffered to pH 5–6) was then determined using an Orion 9409 fluoride electrode and an Orion 9001 single junction reference electrode connected to an Orion 901 ionanalyzer unit. Using this result and the actual weights of catalyst and feed employed in the recycle reactor run, the F content of the alumina bed effluent was calculated assuming complete transfer of the F to the catalyst.

EXAMPLE 1

Three commercial grades of activated alumina were compared. The process used was a Dehy-HF process for LAB production operating continuously on heavy feedstock with recycle of unconverted NP and benzene. The process did not include selective hydrogenation of dehydrogenation products but did include removal of lowboilers from the dehydrogenation products and selective hydrogenation of the alkylation product after the removal of NP. A single fixed bed alumina treater was operated at about 290° C. to remove RF from the liquid stream fed to the NP recovery column. The amount of alumina used was about 0.12 lbs./lb./hr. of treater feed. All process parameters other than the grade of alumina used were essentially the same for each of the three test periods. Analyses of the treater effluents showed that each of the aluminas effectively removed RF from the treated stream. The entire LAB product was recovered in a single distillation fraction, and its $SO_3$ sulfonation color was determined. Colors obtained (expressed in Klett units) are shown in the following table along with corresponding alumina selectivity test results for comparison.

| ALUMINA | ALUMINA TYPE | SELECTIVITY (Br No. Rise) | $SO_3$ COLOR GRADE OF LAB |
|---|---|---|---|
| Alcoa Selexsorb COS | High Selectivity Basic | 0.016 | 46 |
| LaRoche A204-4 | High Selectivity Basic | 0.025 | 60 |
| LaRoche A202-HF | Neutral | 0.048 | 175 |

These results illustrate, for heavy feedstock operations, the greatly improved LAB $SO_3$ sulfonation color obtained using high selectivity basic alumina in the process of this invention, compared to the use of a process which is the same except that a neutral alumina is used in place of the basic alumina. It can also be seen that lower Br No. Rise in the alumina selectivity test is an effective indicator that a particular basic alumina will provide improved LAB $SO_3$ sulfonation color in accordance with this invention.

EXAMPLE 2

Two commercial grades of high selectivity basic alumina were tested as in Example 1 except that the operations employed light feedstock, the temperature of the alumina treater was about 252° C., the amount of alumina used was about 0.11 lbs./lb./hr. of alumina treater feed, and the LAB product was recovered in two distillation fractions. Analysis of the alumina treater effluents showed that each of the aluminas effectively removed RF from the treated stream. Sulfonation color results are shown in the following table, compared to typical results obtained earlier using a neutral alumina in the same type of process.

| | $SO_3$ SULFONATION COLOR OF LAB | |
|---|---|---|
| ALUMINA GRADE | LOWER BOILING FR. | HIGHER BOILING FR. |
| Alcoa Selexsorb COS | 30 | 43 |
| LaRoche A204-4 | 32 | 62 |
| Neutral Alumina | 82 | 181 |

These results illustrate, for light feedstock operations, the greatly improved LAB $SO_3$ sulfonation color obtained by using high selectivity basic alumina in the process of this invention compared to that obtained in a process which is the same except for the use of neutral alumina in place of the basic alumina.

EXAMPLE 3

The process of Example 1 was repeated except that the alumina treater was repiped to treat only the recycle paraffin, and a larger amount of alumina was employed. At this position in the process a lower temperature is encountered by the alumina. Also, hydrogenation of the alkylation product was not included because of operating problems which can occur when RF is allowed to enter that step. The $SO_3$ sulfonation color of the resulting LAB was 51. A separate test determined that the effect upon the LAB $SO_3$ sulfonation color of operating without the hydrogenation step was small under these conditions, not greater than about 3 Klett units. Comparison of this result to that obtained in Example 1 with the Selexsorb alumina shows that the best LAB $SO_3$ sulfonation color obtained using the process of this invention is about equal to that obtained when only the recycle paraffin stream is alumina treated. This is so even though the best high selectivity basic alumina does not completely eliminate the Br No. Rise measured in the alumina selectivity test. During this test, various streams were analyzed for the presence of HF, and HF at objectionable levels was found in many of the process areas left unprotected by the repiping of the alumina treater to the recycle NP stream.

EXAMPLE 4

Various aluminas were subjected to the alumina selectivity test described herein, and the results obtained are shown in the table below.

| ALUMINA TYPE | BASIC METAL | FEED TYPE | BROMINE NUMBER RISE | RATIO |
|---|---|---|---|---|
| Basic | 4% Na₂O | Heavy | 0.016 | 0.64 |
| Basic | 5% Na₂O | Heavy | 0.020 | 0.80 |
| Basic | 3-4% Na₂O | Heavy | 0.025 | 1.00 |
| Basic | 1.5% Na₂O | Heavy | 0.025 | 1.00 |
| Basic | 9% CaO | Heavy | 0.027 | 1.08 |
| Special Neutral | — | Heavy | 0.031 | 1.24 |
| Basic | 5% CaO | Heavy | 0.032 | 1.28 |
| Neutral | — | Heavy | 0.048 | 1.92 |
| Basic | 3-4% Na₂O | Light | 0.009 | 0.43 |
| Basic | 1.2% Na₂O | Light | 0.021 | 1.00 |
| Neutral | — | Light | 0.042 | 2.00 |
| Neutral | — | Light | 0.042 | 2.00 |

These results illustrate the tendency of basic aluminas to give better selectivity than neutral aluminas, the wide range of selectivities exhibited by basic aluminas, the tendency for sodium as the basic metal to give better selectivity than calcium, and the tendency for selectivity to improve as the amount of a basic metal is increased, although exceptions can occur due to structural differences. The "special neutral" alumina included is Alcoa's CDO-200 grade which is described in product literature as having very low Bronsted acidity. While it had better selectivity than other neutral aluminas, its selectivity was lower than that of most of the basic aluminas tested.

EXAMPLE 5

A high selectivity basic alumina, LaRoche A204-4, was subjected to the alumina selectivity test described herein using a heavy feed. The procedure was then repeated using the same lot of feed, except that the alumina bed temperature was reduced to 260° C. The resulting values of Br No. Rise were 0.025 for the standard test conducted at 288° C. and 0.018 for the test conducted at the lower temperature. This illustrates the selectivity advantage of using a lower alumina bed temperature within an acceptable range that provides adequate RF removal.

EXAMPLE 6

A number of alumina treater effluent samples which had been generated in runs of the alumina treater selectivity test described herein were analyzed for their residual F content. The results obtained are shown in the following table.

| ALUMINA | FEED TYPE | RESID. F, PPM |
|---|---|---|
| 1. LaRoche A201 | Light | 0.35 |
| 2. LaRoche A202HF | Light | 0.37 |
| 3. LaRoche A204-1 | Light | 0.30 |
| 4. LaRoche A202HF | Heavy | 0.21 |
| 5. Alcoa Selexsorb COS | Heavy | 0.20 |
| 6. Alcan AA-200S | Heavy | 0.16 |

This illustrates that some basic aluminas (Nos. 3, 5 and 6 above) are comparable to typical neutral aluminas (Nos.1, 2 and 4) in their effectiveness for the removal of RF. Differences would tend to be smaller in a well designed alumina treater as opposed to the very short bed used in the alumina selectivity test.

Although the invention has been described in terms of specific embodiments which are set forth in considerable detail, it should be understood that this description is by way of illustration only and that the invention is not necessarily limited thereto since alternative embodiments and operating techniques will become apparent to those skilled in the art in view of this disclosure. Accordingly, modifications are contemplated which can be made without departing from the scope of this described invention.

We claim:

1. In a process for the preparation of detergent range linear alkylbenzene wherein (1) linear monoolefins are reacted with benzene in the presence of a hydrofluoric acid catalyst, (2) the catalyst is removed to obtain a hydrocarbon mixture, (3) crude alkylbenzene is recovered from said hydrocarbon mixture, and (4) the crude alkylbenzene is then purified to obtain linear alkylbenzene, the improvement which comprises contacting at least a portion of said hydrocarbon mixture comprising crude alkylbenzene with basic alumina under organic fluoride impurities removal conditions, said alumina having a bromine number ratio of not greater than about 1.25 in the alumina selectivity test whereby the formation of darkly colored materials upon $SO_3$-sulfonation of said detergent range linear alkylbenzene is reduced.

2. The process of claim 1 wherein the monoolefins are derived from dehydrogenation of the corresponding normal paraffins.

3. The process of claim 2 comprising contacting crude alkylbenzene with said alumina after step (3).

4. The process of claim 3 comprising separating the unconverted normal paraffins and then contacting said paraffins with basic alumina under organic fluoride impurities removal conditions.

5. The process of claim 3 comprising separating unconverted normal paraffins and then contacting said paraffins with neutral alumina under organic fluoride impurities removal conditions.

6. The process of claim 1 wherein the basic alumina contains at least about 0.5%, by weight, sodium oxide.

7. The process of claim 6 wherein the basic alumina contains from about 3% to about 5%, by weight, sodium oxide.

8. The process of claim 1 wherein the bromine number ratio of the basic alumina is not greater than about 1.0.

9. The process of claim 1 wherein the mixture contacting the basic alumina is at a temperature in the range of from about 200° C. to about 295° C.

10. The process of claim 9 wherein the mixture contacting the basic alumina is at a temperature in the range of from about 230° C. to about 260° C.

11. The process of claim 1 wherein the basic alumina contains at least about 0.5%, by weight, as the oxide, of one or more metals selected from the group consisting of alkali and alkaline earth metals.

12. The process of claim 11 wherein the metal is alkali metal.

13. In a process for the preparation of detergent range linear alkylbenzene wherein (1) linear monoolefins derived from the dehydrogenation of normal paraffins over a platinum catalyst are reacted with benzene in the presence of a hydrofluoric acid catalyst, (2) the catalyst is removed to obtain a hydrocarbon mixture, (3) crude alkylbenzene is recovered from said hydrocarbon mixture, and (4) the crude alkylbenzene is then purified to obtain linear alkylbenzene, the improvement which comprises contacting at least a portion of said hydrocarbon mixture comprising crude alkylbenzene with basic alumina under organic fluoride impurities removal conditions, said alumina having a bromine number ratio of not greater than about 1.25 in the alumina selectivity test whereby the formation of darkly colored materials upon $SO_3$-sulfonation of said detergent range linear alkylbenzene is reduced.

14. The process of claim 13 wherein said hydrocarbon mixture contacting said alumina also comprises benzene.

15. The process of claim 13 wherein the bromine number ratio of said basic alumina is not greater than about 1.0.

16. The process of claim 13 wherein the mixture contacting the basic alumina is at a temperature in the range of from about 200° C. to about 295° C.

17. The process of claim 16 wherein the mixture contacting the basic alumina is at a temperature in the range of from about 230° C. to about 260° C.

18. The process of claim 13 wherein the basic alumina contains at least about 0.5%, by weight, sodium oxide.

19. The process of claim 18 wherein the basic alumina contains from about 3% to about 5%, by weight, sodium oxide.

20. The process of claim 14 wherein the basic alumina contains at least about 0.5%, by weight, sodium oxide.

21. The process of claim 20 wherein the basic alumina contains from about 3% to about 5%, by weight, sodium oxide.

22. In a process for the preparation of detergent range linear alkylbenzene wherein (1) linear monoolefins derived from the dehydrogenation of normal paraffins over a platinum catalyst are reacted with benzene in the presence of a hydrofluoric acid catalyst, (2) the catalyst is removed to obtain a hydrocarbon mixture, (3) crude alkylbenzene is recovered from said hydrocarbon mixture, and,(4) the crude alkylbenzene is then purified to obtain linear alkylbenzene, the improvement which comprises contacting at least a portion of said hydrocarbon mixture comprising crude alkylbenzene from which unreacted benzene has been removed with basic alumina under organic fluoride impurities removal conditions, said alumina having a bromine number ratio of not greater than about 1.25 in the alumina selectivity test whereby the formation of darkly colored materials upon $SO_3$-sulfonation of said detergent range linear alkylbenzene is reduced.

23. The process of claim 22 wherein the bromine number ratio of the basic alumina is not greater than about 1.0.

24. The process of claim 22 Wherein the basic alumina contains at least about 0.5%, by weight, as the oxide, of one or more metals selected from the group consisting of alkali and alkaline earth metals.

25. The process of claim 24 wherein the metal is alkali metal.

26. The process of claim 25 wherein the alkali metal is sodium.

27. The process of claim 26 wherein the sodium content is in the range of from about 3% to about 5%, by weight.

28. The process of claim 22 wherein the mixture contacting the basic alumina is at a temperature in the range of from about 200° C. to about 295° C.

29. The process of claim 28 wherein the mixture contacting the basic alumina is at a temperature in the range of from about 230° C. to about 260° C.

* * * * *